(12) United States Patent
Santini et al.

(10) Patent No.: US 12,106,502 B2
(45) Date of Patent: Oct. 1, 2024

(54) SYSTEM AND METHOD FOR DETERMINING DEPTH PERCEPTION IN VIVO IN A SURGICAL ROBOTIC SYSTEM

(71) Applicant: Vicarious Surgical Inc., Waltham, MA (US)

(72) Inventors: Fabrizio Santini, Arlington, MA (US); Sammy Khalifa, Medford, MA (US)

(73) Assignee: Vicarious Surgical Inc., Waltham, MA (US)

( * ) Notice: Subject to any disclaimer, the term of this patent is extended or adjusted under 35 U.S.C. 154(b) by 45 days.

(21) Appl. No.: 17/882,226

(22) Filed: Aug. 5, 2022

(65) Prior Publication Data

US 2022/0383531 A1 Dec. 1, 2022

Related U.S. Application Data

(63) Continuation of application No. PCT/US2021/016999, filed on Feb. 8, 2021.

(60) Provisional application No. 62/971,097, filed on Feb. 6, 2020.

(51) Int. Cl.
*A61B 34/30* (2016.01)
*G06T 7/593* (2017.01)
*H04N 13/239* (2018.01)
*H04N 23/67* (2023.01)

(52) U.S. Cl.
CPC .............. *G06T 7/593* (2017.01); *A61B 34/30* (2016.02); *H04N 13/239* (2018.05); *H04N 23/67* (2023.01); *G06T 2207/10028* (2013.01); *G06T 2207/20084* (2013.01); *G06T 2207/30004* (2013.01)

(58) Field of Classification Search
CPC ........... G06T 7/593; G06T 2207/10028; G06T 2207/20084; G06T 2207/30004; A61B 34/30; H04N 13/239; H04N 23/67
See application file for complete search history.

(56) References Cited

U.S. PATENT DOCUMENTS 10,200,623 B1 * 2/2019 Baldwin ................ H04N 23/63
10,916,035 B1 * 2/2021 Kroeger ............... G05D 1/0212
(Continued)

FOREIGN PATENT DOCUMENTS

| CN | 110600122 A | 12/2019 |
|---|---|---|
| JP | 2014-175965 A | 9/2014 |
| WO | 2018/087083 A1 | 5/2018 |

OTHER PUBLICATIONS

International Search Report and Written Opinion for Application No. PCT/US2021/016999, dated Apr. 29, 2021, 10 pages.
(Continued)

*Primary Examiner* — Mohamed A. Wasel
(74) *Attorney, Agent, or Firm* — McCarter & English, LLP

(57) ABSTRACT

A system and method for generating a depth map from image data in a surgical robotic system that employs a robotic subsystem having a camera assembly with first and second cameras for generating image data. The system and method generates based on the image data a plurality of depth maps, and then converts the plurality of depth maps into a single combined depth map having distance data associated therewith. The system and method can then control the camera assembly based on the distance data in the single combined depth map.

28 Claims, 6 Drawing Sheets

(56) References Cited

U.S. PATENT DOCUMENTS

| | | | |
|---|---|---|---|
| 2009/0248036 A1* | 10/2009 | Hoffman | A61B 1/00149 |
| | | | 606/130 |
| 2009/0248041 A1* | 10/2009 | Williams | A61B 18/22 |
| | | | 606/130 |
| 2014/0018819 A1 | 1/2014 | Raj et al. | |
| 2014/0243597 A1* | 8/2014 | Weisenburgh, II | A61B 1/00158 |
| | | | 600/109 |
| 2017/0143429 A1* | 5/2017 | Richmond | A61B 34/37 |
| 2018/0035017 A1 | 2/2018 | Kim | |
| 2018/0087083 A1 | 3/2018 | Sallin et al. | |
| 2019/0037202 A1 | 1/2019 | Uemori et al. | |
| 2019/0182475 A1 | 6/2019 | Wu | |
| 2019/0200870 A1* | 7/2019 | Ortega-Quijano | A61B 5/0084 |
| 2019/0327393 A1* | 10/2019 | Yang | H04N 5/2226 |
| 2019/0333627 A1 | 10/2019 | Johnson | |
| 2019/0380566 A1 | 12/2019 | Charles et al. | |
| 2020/0169673 A1* | 5/2020 | King | G16H 40/63 |
| 2023/0177703 A1* | 6/2023 | Fathollahi Ghezelghieh | G06V 10/7715 |
| | | | 382/103 |

OTHER PUBLICATIONS

International Preliminary Report on Patentability for Application No. PCT/US2021/016999, dated Jul. 28, 2022, 9 pages.
Nazzal, How astronomers measure distance to stars using parallax. Retrieved online at: referenceframe.net/astronomy/how-astronomers-measure-distance-to-stars-using-parallaz/. 35 pages, Dec. 21, 2017.
Canadian Office Action for Application No. 3,167,157, dated Nov. 10, 2023, 12 pages.
Wikipedia, Binocular disparity. Retrieved online at: https://en.wikipedia.org/wiki/Binocular_disparity#:~:text=Binocular%20disparity%20refers%20to%20the,dimensional%20retinal%20images%20in%20stereopsis. 5 pages, (2022).
European Office Action for Application No. 21750345.7, dated Jan. 30, 2024, 13 pages.

* cited by examiner

SYSTEM AND METHOD FOR DETERMINING DEPTH PERCEPTION IN VIVO IN A SURGICAL ROBOTIC SYSTEM

RELATED APPLICATION

The present invention is a continuation of International Patent Application Serial No. PCT/US2021/016999, filed on Feb. 8, 2021, which claims priority to U.S. provisional patent application Ser. No. 62/971,097, entitled DEPTH PERCEPTION IN VIVO, filed on Feb. 6, 2020, the contents of each of the above applications being herein incorporated by reference.

BACKGROUND OF THE INVENTION

The present invention is related to surgical robotic systems, and more specifically is related to surgical robotic systems employing a camera assembly.

Minimally invasive surgery (MIS) has a proven to be a benefit to patient outcomes when compared to open procedures, in which surgeons operate by hand through a large incision, as it significantly decreases patient recovery times, risk of infection, rates of future herniation, and allows more outpatient surgeries to be performed.

Despite the advent of manual and robotic MIS systems, open procedures remain the standard of care for many indications due to the complexity of the procedures as well as the general limitations of current MIS solutions. These limitations include the amount of training and practice required to become proficient at MIS as well as limited abdominal access from one insertion location.

The advanced surgical system disclosed in U.S. Pat. No. 10,285,765 entitled Virtual Reality Surgical Device, U.S. Patent Publication No. 2019/0142531 entitled Virtual Reality Wrist Assembly, and U.S. Patent Publication No. 2019/0076199 entitled Virtual Reality Surgical Camera System, is capable of reaching any part of the abdomen with one MIS incision. The natural interfaces and poseable viewpoint create a surgical system that requires minimal instrument-specific training. The surgeon operates as if the robot were her own hands and eyes and, combined with high quality manufacturing and lower per-system costs, enables surgeons to focus on providing quality care to patients.

One of the biggest issues with conventional MIS systems is that injuries can occur outside of the visual field of the operator. Generating detailed three-dimensional (3D) maps of the surgical stage enables the system to actively prevent collisions and help the surgeon plan an optimal surgical path for the robot components, such as the robotic arms.

Furthermore, depth data allows for use of an autonomous surgical robot that can deftly interact with human tissues while executing navigational and surgical procedures inside the patient in a safe and efficient manner. An intelligent and autonomous surgical system, capable of performing basic surgical procedures, requires detailed three-dimensional knowledge of a patient's interior. As such, knowledge of depth is a cornerstone of this goal.

The robotic surgical system disclosed in the aforementioned publications blends miniaturized robotics and augmented reality. In some embodiments the system comprises two eight degrees-of-freedom (DOF) robotic arms plus a stereoscopic camera assembly or head, which is inserted through a single incision and unfurled inside the patient's abdominal cavity. The surgeon controls the robotic arms with two six-axis hand-held controllers while visualizing the complete surgical state via the robotic head and a virtual reality headset.

While the unique architecture of this system provides opportunities and capabilities not realized by any other surgical methods or systems, the surgeon can only make use of visual feedback of the patient's interior. The brain naturally uses a variety of low-level and high-level sources to obtain reliable and robust distance estimations as humans heavily rely on depth cues to interact with the environment. Making these cues accessible through the robotic head enhance the surgeon's capabilities creating a much richer and effective experience.

However, available conventional and commercially augmented reality and virtual reality systems are not capable of providing sufficient depth information to guarantee an accurate visual representation and feedback to the surgeon.

SUMMARY OF THE INVENTION

The present invention is directed to a surgical robotic system that employs a depth perception subsystem for generating a plurality of depth maps, and then combining or merging the depth maps into a single depth map. The depth perception subsystem also generates a series of confidence values that are associated with the distance data in the single combined depth map. The confidence values are an indication of the confidence or the likelihood that the distance data associated with a selected point or portion of the depth map is correct or accurate. The depth perception subsystem generates depth maps associated with the cameras of the camera assembly. Specifically, the depth perception subsystem generates depth maps associated with the autofocus mechanisms of the cameras, the parallax data associated with each camera, and the disparity between the image data from each camera. The depth perception subsystem then processes all of the depth maps to produce the combined single depth map. The depth map data and the confidence values can be employed by the system to move one or more components of the robotic subsystem.

The present invention is directed to a surgical robotic system, comprising a robotic subsystem having a camera assembly having first and second cameras for generating image data, and a computing unit having a processor for processing the image data, control unit for controlling the robotic subsystem, and a depth perception subsystem for receiving the image data generated by the first and second cameras and for generating, based on the image data, a plurality of depth maps, and then converting the plurality of depth maps into a single combined depth map having distance data associated therewith. The robotic subsystem further comprises a plurality of robotic arms and a motor unit for controlling movement of the plurality of robotic arms and the camera assembly. The control unit employs the distance data associated with the single combined depth map to control one of the camera assembly and the robotic arms. The depth perception subsystem further comprises a depth map conversion unit for receiving the plurality of depth maps, and then converting the depth maps into the single combined depth map. The depth map conversion unit generates the single combined depth map using a regional convolution neural network (R-CNN) technique.

Further, each of the first and second cameras comprises an image sensor for receiving optical data and for generating the image data in response thereto, a lens and optical system having one or more lens elements optically coupled with the image sensor for focusing the optical data onto the image sensor, and an autofocus mechanism associated with the lens and optical system for automatically adjusting the one or more lens elements and for generating autofocus data.

The depth perception subsystem of the present invention includes one or more of or any selected combination of a first autofocus conversion unit for receiving the autofocus data from the first camera and for converting the autofocus data into a first autofocus depth map; a second autofocus conversion unit for receiving the autofocus data from the second camera and for converting the autofocus data into a second autofocus depth map; a first parallax conversion unit for receiving image data from the first camera and for converting the image data into a first parallax depth map; a second parallax conversion unit for receiving image data from the second camera and for converting the image data into a second parallax depth map; and a disparity conversion unit for receiving image data from the first camera and image data from the second camera and then generating in response thereto a disparity depth map.

The first and second parallax units can be configured to acquire first and second successive images in the image data and then to measure an amount that each portion of the first image moves relative to the second image. Further, each of the first and second parallax conversion units can include a segmentation unit for receiving the image data from the respective camera and dividing the image data into a plurality of segments, and then in response to the plurality of segments generating shifted image data; a movement determination unit for receiving the position data from the respective camera and then generating in response thereto camera movement data indicative of the position of the camera; and a distance conversion unit for receiving the image data and the camera movement data and then converting the image data and the camera movement data into the respective parallax depth map. The distance conversion unit employs a regional convolutional neural network (R-CNN) technique to generate the respective parallax depth map. Further, the disparity conversion unit analyzes a disparity between an image in the image data received from the first camera and an image in the image data received from the second camera.

The depth perception subsystem further comprises a depth map conversion unit for receiving the first autofocus depth map, the second autofocus depth map, the first parallax depth map, the second parallax depth map, and the disparity depth map, forming received depth maps, and then converting the received depth maps into the single combined depth map. Also, the depth map conversion unit includes a depth map generation unit for receiving the received depth maps and then converting the received depth maps into the single combined depth map, and a confidence value generation unit for generating from the received depth maps a confidence value associated with each of the distance values associated with each point of the single combined depth map. The confidence value is indicative of a confidence in the distance values associated with the single combined depth map.

The present invention is also directed to a method for generating a depth map from image data in a surgical robotic system, comprising providing a robotic subsystem having a camera assembly having first and second cameras for generating image data, generating, based on the image data from the first and second cameras, a plurality of depth maps, converting the plurality of depth maps into a single combined depth map having distance data associated therewith, and controlling the camera assembly based on the distance data in the single combined depth map.

The method also includes one or more of, or any combination of, converting the autofocus data from the first camera into a first autofocus depth map; converting the autofocus data from the second camera into a second autofocus depth map; converting the image data from the first camera into a first parallax depth map; converting the image data from the second camera into a second parallax depth map; and generating from the image data from the first camera and the image data from the second camera a disparity depth map.

The method also includes receiving the first autofocus depth map, the second autofocus depth map, the first parallax depth map, the second parallax depth map, and the disparity depth map, forming received depth maps, and then converting the received depth maps into the single combined depth map. Further, the method includes generating from the received depth maps a confidence value associated with each of the distance values associated with each point of the single combined depth map. The confidence value is indicative of a confidence in the distance values associated with the single combined depth map.

BRIEF DESCRIPTION OF THE DRAWINGS

These and other features and advantages of the present invention will be more fully understood by reference to the following detailed description in conjunction with the attached drawings in which like reference numerals refer to like elements throughout the different views. The drawings illustrate principals of the invention and, although not to scale, show relative dimensions.

DETAILED DESCRIPTION

Figure 1:
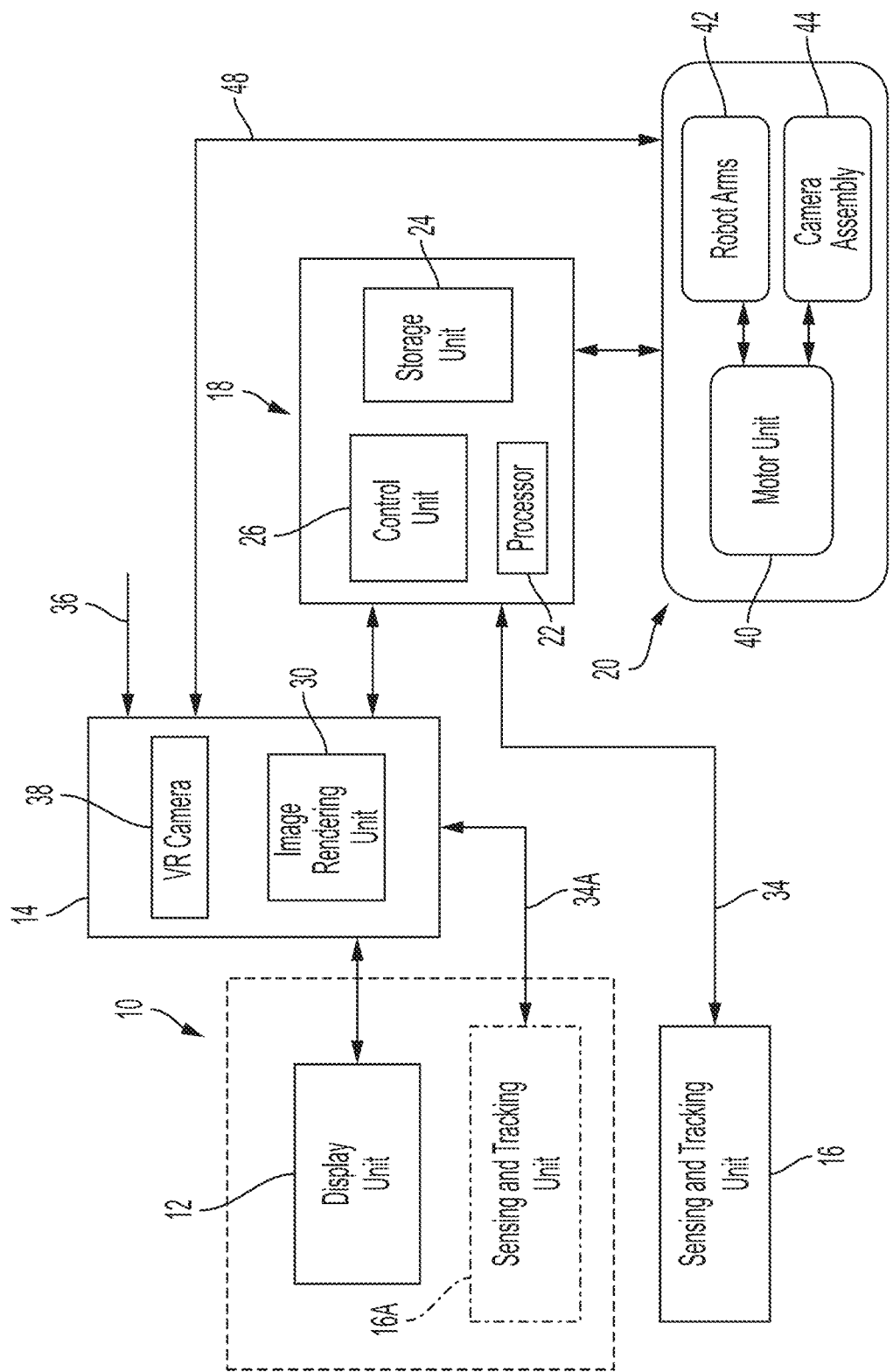
FIG. 1 is a schematic block diagram illustration of a surgical robotic system suitable for use with the present invention.

In the following description, numerous specific details are set forth regarding the systems and methods of the present invention and the environment in which the system and method may operate, in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that any examples provided below are merely illustrative and are not to be construed in a limiting manner, and that it is contemplated by the present inventors that other systems, apparatuses, and/or methods can be employed to implement the teachings of the present invention and that are deemed to be within the scope of the present invention.

While the systems and methods of the present invention can be designed for use with one or more surgical robotic systems employed as part of a virtual reality surgery, the system of the present invention may be employed in connection with any type of surgical system, including for example robotic surgical systems, straight-stick type surgical systems, and laparoscopic systems. Additionally, the system of the present invention may be used in other non-surgical systems, where a user requires access to a myriad of information, while controlling a device or apparatus.

The systems and methods disclosed herein can be incorporated and utilized with the robotic surgical device and associated system disclosed for example in U.S. Pat. No. 10,285,765 and in PCT patent application Ser. No. PCT/US20/39203, and/or with the camera system disclosed in U.S. Publication No. 2019/0076199, where the content and teachings of all of the foregoing applications and publications are herein incorporated by reference. The surgical robot system that forms part of the present invention can comprise a surgical system that includes a user workstation, a robot support system (RSS), a motor unit, and an implantable surgical robot that includes one or more robot arms and one or more camera assemblies. The implantable robot arms and camera assembly can form part of a single support axis robot system or can form part of a split arm architecture robot system.

The robot arms can have portions or regions that can be associated with movements associated with the shoulder, elbow, wrist and fingers of the user. For example, the robotic elbow can follow the position and orientation of the human elbow, and the robotic wrist can follow the position and orientation of the human wrist. The robot arms can also have associated therewith end regions that can terminate in end-effectors that follow the movement of one or more of fingers of the user, such as for example the index finger as the user pinches together the index finger and thumb. While the arms of the robot follow movement of the arms of the user, the robot shoulders are fixed in position. In one embodiment, the position and orientation of the torso of the user is subtracted from the position and orientation of the user's arms. This subtraction allows the user to move his or her torso without the robot arms moving. The robot arms can be configured to reach all areas of a surgical site, and can work in different configurations and in tight spaces.

The present invention is directed to a surgical robotic system that employs a depth perception subsystem for generating a plurality of depth maps, and then combining or merging the depth maps into a single combined depth map. The depth perception subsystem also generates a series of confidence values that are associated with the distance data in the single combined depth map. The confidence values are an indication of the confidence or the likelihood that the distance data associated with a selected point or portion of the depth map is correct or accurate. The depth perception subsystem generates depth maps associated with the cameras of the camera assembly. Specifically, the depth perception subsystem generates depth maps associated with the autofocus mechanisms of the cameras, the parallax data associated with each camera, and the disparity between the image data from each camera. The depth perception subsystem then processes all of the depth maps to produce the combined single depth map. The depth map data and the confidence values can be employed by the system to move one or more components of the robotic subsystem.

FIG. 1 is a schematic block diagram description of a surgical robotic system 10 according to the teachings of the present invention. The system 10 includes a display device or unit 12, a virtual reality (VR) computing unit 14, a sensing and tracking unit 16, a computing unit 18, and a robotic subsystem 20. The display unit 12 can be any selected type of display for displaying information, images or video generated by the VR computing unit 14, the computing unit 18, and/or the robotic subsystem 20. The display unit 12 can include for example a head-mounted display (HMD), a screen or display, a three-dimensional (3D) screen, and the like. The display unit can also include an optional sensor and tracking unit 16A, such as can be found in commercially available head mounted displays. The sensing and tracking units 16 and 16A can include one or more sensors or detectors that are coupled to a user of the system, such as for example a nurse or a surgeon. The sensors can be coupled to the arms of the user and if a head-mounted display is not used, then additional sensors can also be coupled to a head and/or neck region of the user. The sensors in this arrangement are represented by the sensor and tracking unit 16. If the user employs a head-mounted display, then the eyes, head and/or neck sensors and associated tracking technology can be built-in or employed within that device, and hence form part of the optional sensor and tracking unit 16A. The sensors of the sensor and tracking unit 16 that are coupled to the arms of the surgeon can be preferably coupled to selected regions of the arm, such as for example the shoulder region, the elbow region, the wrist or hand region, and if desired the fingers. The sensors generate position data indicative of the position of the selected portion of the user. The sensing and tracking units 16 and/or 16A can be utilized to control the camera assembly 44 and the robotic arms 42 of the robotic subsystem 20. The position data 34 generated by the sensors of the sensor and tracking unit 16 can be conveyed to the computing unit 18 for processing by a processor 22. The computing unit 18 can determine or calculate from the position data the position and/or orientation of each portion of the surgeon's arm and convey this data to the robotic subsystem 20. According to an alternate embodiment, the sensing and tracking unit 16 can employ sensors coupled to the torso of the surgeon or any other body part. Further, the sensing and tracking unit 16 can employ in addition to the sensors an Inertial Momentum Unit (IMU) having for example an accelerometer, gyroscope, magnetometer, and a motion processor. The addition of a magnetometer is standard practice in the field as magnetic heading allows for reduction in sensor drift about the vertical axis. Alternative embodiments also include sensors placed in surgical material such as gloves, surgical scrubs, or a surgical gown. The sensors may be reusable or disposable. Further, sensors can be disposed external of the user, such as at fixed locations in a room, such as an operating room. The external sensors can generate external data 36 that can be processed by the computing unit and hence employed by the system 10. According to another embodiment, when the display unit 12 is a head mounted device that employs an associated sensor and tracking unit 16A, the device generates tracking and position data 34A that is received and processed by the VR computing unit 14. Further, the sensor and tracking unit 16 can include if desired a hand controller.

In the embodiment where the display is a HMD, the display unit 12 can be a virtual reality head-mounted display, such as for example the Oculus Rift, the Varjo VR-1 or the HTC Vive Pro Eye. The HMD can provide the user with a display that is coupled or mounted to the head of the user, lenses to allow a focused view of the display, and a sensor and/or tracking system 16A to provide position and orientation tracking of the display. The position and orientation sensor system can include for example accelerometers, gyroscopes, magnetometers, motion processors, infrared tracking, eye tracking, computer vision, emission and sensing of alternating magnetic fields, and any other method of tracking at least one of position and orientation, or any combination thereof. As is known, the HMD can provide image data from the camera assembly 44 to the right and left eyes of the surgeon. In order to maintain a virtual reality experience for the surgeon, the sensor system can track the position and orientation of the surgeon's head, and then relay the data to the VR computing unit 14, and if desired to the computing unit 18. The computing unit 18 can further adjust the pan and tilt of the camera assembly 44 of the robotic subsystem 20 via the motor unit 40 so as to follow the movement of the user's head.

The sensor or position data generated by the sensors if associated with the display unit 12 can be conveyed to the computing unit 18 either directly or via the VR computing unit 14. Likewise, the tracking and position data 34 generated by the other sensors in the system, such as from the sensing and tracking unit 16 that can be associated with the user's arms and hands, can be conveyed to the computing unit 18. The tracking and position data 34, 34A can be processed by the processor 22 and can be stored for example in the storage unit 24. The tracking and position data 34, 34A can also be used by the control unit 26, which in response can generate control signals for controlling one or more portions of the robotic subsystem 20. The robotic subsystem 20 can include a user workstation, a robot support system (RSS), a motor unit 40, and an implantable surgical robot that includes one or more robot arms 42 and one or more camera assemblies 44. The implantable robot arms and camera assembly can form part of a single support axis robot system, such as that disclosed and described in U.S. Pat. No. 10,285,765, or can form part of a split arm architecture robot system, such as that disclosed and described in PCT patent application no. PCT/US20/39203, the contents of which are incorporated by reference.

The control signals generated by the control unit 26 can be received by the motor unit 40 of the robotic subsystem 20. The motor unit 40 can include a series of servo motors that are configured for driving separately the robot arms 42 and the cameras assembly 44. The robot arms 42 can be controlled to follow the scaled-down movement or motion of the surgeon's arms as sensed by the associated sensors. The robot arms 42 can have portions or regions that can be associated with movements associated with the shoulder, elbow, wrist and fingers of the user. For example, the robotic elbow can follow the position and orientation of the human elbow, and the robotic wrist can follow the position and orientation of the human wrist. The robot arms 42 can also have associated therewith end regions that can terminate in end-effectors that follow the movement of one or more of fingers of the user, such as for example the index finger as the user pinches together the index finger and thumb. While the arms of the robot follow movement of the arms of the user, the robot shoulders are fixed in position. In one embodiment, the position and orientation of the torso of the user is subtracted from the position and orientation of the user's arms. This subtraction allows the user to move his or her torso without the robot arms moving.

The robot camera assembly 44 is configured to provide the surgeon with image data 48, such as for example a live video feed of an operation or surgical site, as well as enable a surgeon to actuate and control the cameras constituting the camera assembly 44. The camera assembly 44 preferably includes a pair of cameras, the optical axes of which are axially spaced apart by a selected distance, known as the inter-camera distance, so as to provide a stereoscopic view of the surgical site. The surgeon can control the movement of the cameras either through movement of a head mounted display or via sensors coupled to the head of the surgeon, or by using a hand controller or sensors tracking the user's head or arm motions, thus enabling the surgeon to obtain a desired view of an operation site in an intuitive and natural manner. The cameras are movable in multiple directions, including for example in the yaw, pitch and roll directions, as is known. The components of the stereoscopic cameras can be configured to provide a user experience that feels natural and comfortable. In some embodiments, the interaxial distance between the cameras can be modified to adjust the depth of the operation site perceived by the user.

The camera assembly 44 is actuated by the movement of the surgeon's head. For example, during an operation, if the surgeon wishes to view an object located above the current field of view, the surgeon looks in the upward direction, which results in the stereoscopic cameras being rotated upward about a pitch axis from the user's perspective. The image or video data 48 generated by the camera assembly 44 can be displayed on the display unit 12. If the display unit 12 is a head-mounted display, the display can include built-in tracking and sensor systems that obtain raw orientation data for the yaw, pitch and roll directions of the HMD as well as positional data in Cartesian space (x, y, z) of the HMD. However, alternative tracking systems may be used to provide supplementary position and orientation tracking data of the display in lieu of or in addition to the built-in tracking system of the HMD. An example of a camera assembly suitable for use with the present invention includes the camera assemblies disclosed in U.S. Pat. No. 10,285,765 and U.S. Publication No, 2019/0076199, to the assignee hereof, the contents of which are incorporated herein by reference.

The image data 48 generated by the camera assembly 44 can be conveyed to the virtual reality (VR) computing unit 14 and can be processed by the VR or image rendering unit 30. The image data 48 can include still photographs or image data as well as video data. The VR rendering unit 30 can include suitable hardware and software for processing the image data and then rendering the image data for display by the display unit 12, as is known in the art. Further, the VR rendering unit 30 can combine the image data received from the camera assembly 44 with information associated with the position and orientation of the cameras in the camera assembly, as well as information associated with the position and orientation of the head of the surgeon. With this information, the VR rendering unit 30 can generate an output video or image rendering signal and transmit this signal to the display unit 12. That is, the VR rendering unit 30 renders the position and orientation readings of the hand controllers and the head position of the surgeon for display in the display unit, such as for example in a HMD worn by the surgeon.

The VR computing unit 14 can also include a virtual reality (VR) camera unit 38 for generating one or more virtual reality (VR) cameras for use or emplacement in the VR world that is displayed in the display unit 12. The VR camera unit can generate one or more virtual cameras in a virtual world, and which can be employed by the system 10 to render the images for the head-mounted display. This ensures that the VR camera always renders the same views that the user wearing the head-mounted display sees to a cube map. In one embodiment, a single VR camera can be used and in another embodiment separate left and right eye VR cameras can be employed to render onto separate left and right eye cube maps in the display to provide a stereo view. The FOV setting of the VR camera can self-configure itself to the FOV published by the camera assembly 44. In addition to providing a contextual background for the live camera views or image data, the cube map can be used to generate dynamic reflections on virtual objects. This effect allows reflective surfaces on virtual objects to pick up reflections from the cube map, making these objects appear to the user as if they're actually reflecting the real world environment.

The robot arms 42 can be composed of a plurality of mechanically linked actuation sections or portions that can be constructed and combined for rotational and/or hinged movement, so as to emulate different portions of the human arm, such as for example the shoulder region, elbow region, and wrist region of the arm. The actuator sections of the robot arm are constructed to provide cable-driven, rotational movement for example, but within the confines of reasonable rotational limits. The actuator sections are configured to provide maximum torque and speed with minimum size.

The present invention is directed to generating and providing depth perception related data (e.g., distance data and/or depth map data) to the robotic subsystem, such that the data can be used by the surgeon to assist in controlling movement of one or more components, such as the robotic arms or cameras, of the subsystem. The depth perception related data is important since it enables the surgeon to determine the amount of movement that the robot can safely perform at a surgical site prior to and during a surgical procedure. Additionally, the data can be used for automated motion without the surgeon. The present invention can also employ software and hardware (e.g., processor, memory, storage, and the like) to calculate or determine three-dimensional (3D) distance maps, or depth maps, from multiple different data and image sources, including for example lens focus data, image data, image disparity data, and image parallax related data. According to other embodiments, other types of depth cues can be used as inputs to the depth perception subsystem 50 of the present invention.

The present invention can employ various computing elements and sensors to determine or extract depth and related distance information. There are a variety of hardware and software that can be used with the system of the present invention to extract depth perception information or distance data. For example, hardware sensors such as structured light or time-of-flight sensors measure changes in a physical parameter to estimate distance. Software sensors can be used to infer distance by analyzing specific features in one or more images in time and space. The system can employ disparity, epipolar geometry, structure-from-motion, and other techniques to generate or convert input images or other types of data into depth related data. Although the system of the present invention can extract depth related information from a single cue or source, the system of the present invention can also consider additional inputs or sources of data when constructing the final combined three-dimensional (3D) depth map. The final combined depth map of the present invention in essence combines a plurality of lower quality depth maps into a single, final combined depth map of any selected scene, such as for example the inside of a human body, that is more robust to noise, occlusion, and ambiguity.

Figure 2:
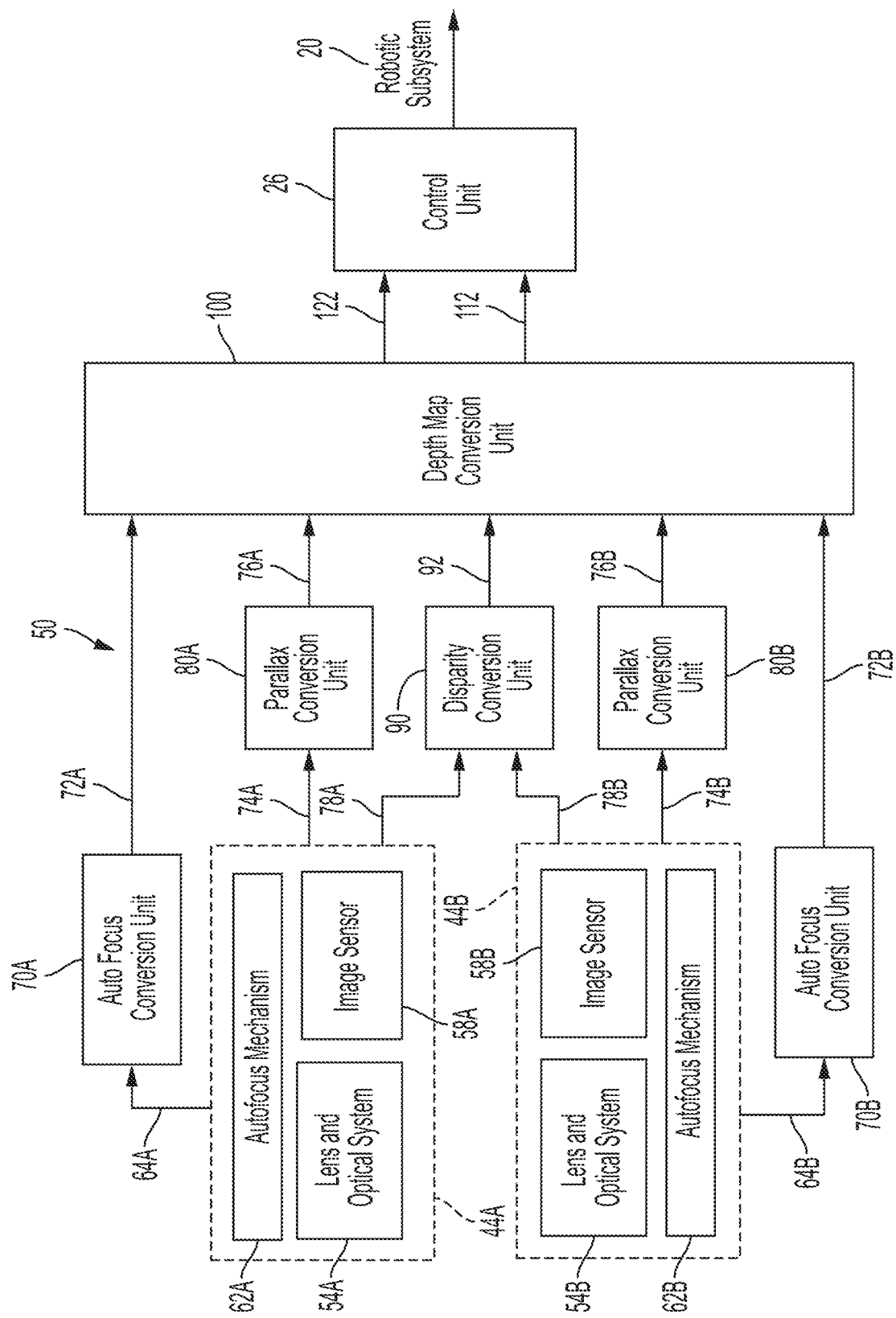
FIG. 2 is a schematic illustration of the depth perception subsystem according to the teachings of the present invention.

The computing unit 18 of the surgical robotic system 10 can include a depth perception subsystem 50, as shown for example in FIG. 2. The depth perception subsystem 50 can be configured to interact with one or more components of the robotic subsystem 20, such as for example the camera assembly 44 and robotic arms 42. The camera assembly 44 can include a pair of stereoscopic cameras, including for example the left camera 44A and the right camera 44B. The left camera 44A can include for example, among many components, a lens and optical system 54A that includes one or more lenses and associated optical elements for receiving optical or image information. The camera 44A can also include an image sensor 58A for capturing optical or image data and an autofocus mechanism 62A for providing autofocus capabilities to the camera. The autofocus mechanism 62A interacts with and automatically changes or adjusts the optics, such as a lens, in the lens and optical system 54A to focus an image on the image sensor 58A. The image sensor surface can typically correspond to the focal plane. Similarly, the right camera 44B can include a lens and optical system 54B that includes one or more lenses and associated optical elements. The camera 44B can also include an image sensor 58B for capturing optical or image data and an autofocus mechanism 62B for providing autofocus capabilities to the camera.

The illustrated cameras 44A, 44B having auto-focusing capabilities can provide information that can be converted into an initial rough depth map of the areas directly monitored by the camera. As such, each camera 44A, 44B constantly monitors an input stream of image data from the image sensors 58A, 58B in order to maintain the observed environment or objects in focus. For each image portion in the image data stream, a subset of pixels of the image can be maintained in focus by the corresponding image sensor. As is known, the autofocus mechanism can generate an effort signal, which are the adjustments requested by the autofocus hardware and software, that can be converted into a control signal that can be used to change the geometry of the optical system mechanically or electrically. Further, for a given image, any subset of pixels that are in focus can be associated with the control signal. The control signal can be converted to an approximate depth by the autofocus conversion unit 70A, 70B, thereby generating a depth map of the pixels in focus.

The illustrated depth perception subsystem 50 can further include an autofocus conversion unit 70A for receiving autofocus data 64A generated by the autofocus mechanism 62A. The autofocus conversion unit 70A serves to convert the autofocus data into distance data, which can be displayed as or form part of a depth map 72A. As used herein, the term "depth map" or "distance map" is intended to include an image, image channel, or map that contains information relating to or about the distance between the surfaces of one or more objects or images from a selected viewpoint or point of view in an overall scene. The depth map can be created from a source image or image data and can be presented in any selected color, such as for example grayscale, and can include variations or hues of one or more colors where each variation or hue corresponds to various or different distances of the images or objects from the viewpoint in the overall scene. Similarly, the autofocus mechanism 62B generates autofocus data that is received by the autofocus conversion unit 70B. In response, the autofocus conversion unit 70B converts the autofocus data into distance data, which can also be displayed as or form part of a separate depth map 72B. In some embodiments, the focal depth can be purposely varied over time to generate a more detailed depth map of different pixels.

The depth perception subsystem 50 can further include parallax conversion units 80A and 80B for converting image data into distance data. Specifically, the left and right cameras 44A, 44B generate camera data 74A, 74B, respectively, which can include for example image data and camera position data, that is transferred to and received by the parallax conversion units 80A, 80B, respectively, and which in turn converts the data into distance data that can form part of separate depth maps 76A, 76B. As is known, the parallax effect is normally present in both natural and artificial optical systems and can make objects that are farther away from the image sensor appear to move more slowly than objects that are closer to the image sensor when moving the image sensor. In some embodiments, a measurement of the parallax effect is accomplished by measuring, for two images taken at successive intervals, how much each portion of the image moved relative to its counterpart in the previous interval. The more a portion of the image has moved between intervals, the closer it is to the camera.

Figure 3:
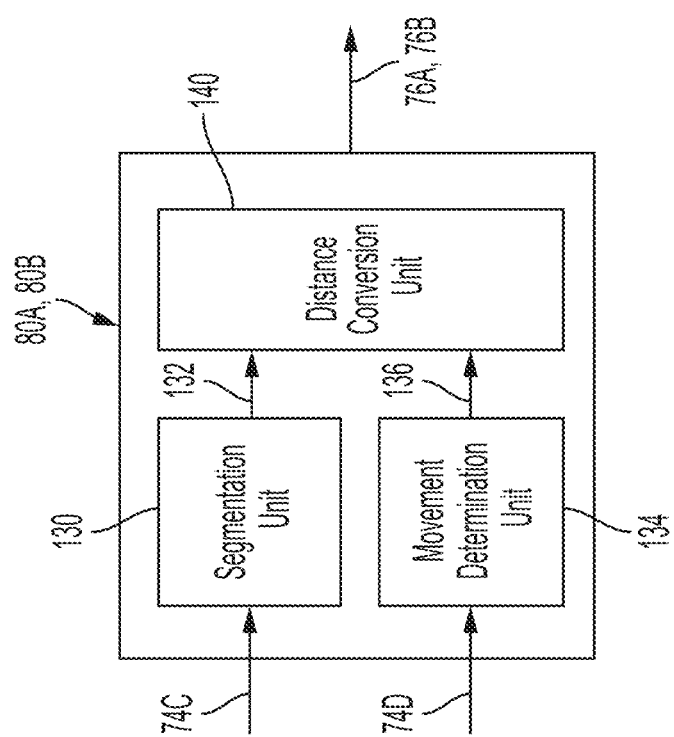
FIG. 3 is a schematic block diagram of the parallax conversion unit of the depth perception subsystem of the present invention.

The specifics of the parallax conversion units 80A, 80B are shown for example in FIG. 3. The parallax conversion units 80A and 80B are the same, and hence the description of only one of the parallax conversion units 80A is described below for purposes of simplicity and clarity. The camera data 74A generated by the camera 44A can include image data 74C and camera position data 74D. The camera position data 74D corresponds to the vertical and horizontal position of the camera as measured by onboard sensors and electronics, or based on commanded position. The image data 74C is introduced to and received by a segmentation unit 130. The segmentation unit 130 divides the image data 74C into a plurality of patches or segments, and then by comparing sets of typically successive images within the image data generates in response thereto shifted image data 132. The camera position data 74D generated by the camera 44A is then received by a movement determination unit 134 that determines the position of the camera and then generates camera movement data 136. The camera movement data 136 is related to the amount of movement or degrees of rotation of the camera, as measured by the onboard sensors, estimated based upon kinematics, or simply estimated based upon commands. The shifted image data 132 and the movement data 136 are then introduced to a distance conversion unit that converts the two types of input data 132, 136 into distance data, which can be represented in the form of a separate depth map 76A. An example of how to determine distance data from image data is disclosed in Active estimation of distance in a robotic system that replicates human eye movement, Santini et al, Robotics and Autonomous Systems, August 2006, the contents of which are herein incorporated by reference.

The distance conversion unit 140 can employ known processing techniques, such as for example a layered regional convolutional neural network (R-CNN) technique. For example, according to one embodiment, training data for the network is generated using pairs of images selected from the image data. Further, the segmentation unit 130 can segment an image, for example an image taken at time t, into smaller image segments. For each image segment, a likely location on an image from the same image sensor but at a different time, for example at time t+1, is calculated using a normalized cross-correlation technique. Since the depth perception subsystem 50 can easily determine the motion actuated during the foregoing time intervals and the difference in location of the image segment between and after the motion, the distance of the 3D points included in the image segment can be calculated or determined via known optical considerations and known analytical formulations and techniques.

With reference again to FIG. 2, the depth perception subsystem 50 further includes a disparity conversion unit 90 that converts image data 78A received from the camera 44A and image data 78B received from the camera 44B into distance data, which can form part of a depth map 92. The disparity conversion unit 90 analyzes the differences or disparity between the images in the image data received from the cameras 44A, 44B. Specifically, the disparity conversion unit 90 analyzes the same image segment of each input image and determines the differences therebetween. The differences between the images recorded by the optical systems and image sensors of the cameras 44A, 44B by observing a scene from different points of view can be used in conjunction with the known geometry and arrangement of the optical systems of the cameras to convert disparity information into distance information. According to one embodiment, the disparity between the images from the left and right cameras 44A, 44B are calculated using an appropriately layered regional convolutional neural network (R-CNN) which considers and processes all the pixels from the images at the same time. The disparity conversion unit 90, for example, can be trained using images from each camera 44A, 44B selected from real time image feeds. Alternatively, in some embodiments, the disparity can be calculated using a formula. In these embodiments, the disparity value (d) can be converted into depth value (Z) by the following formula:

$$Z=R*f/d$$

where f is the focal length of the camera and T is the baseline distance between the cameras.

The depth map or distance data 92 generated by the disparity conversion unit 90 and which corresponds to the input image data under consideration can be generated and refined by using epipolar geometry. For example, the likely location of point A on the left image received by the left camera 44A can be estimated on the right image received from the right camera 44B. A normalized cross-correlation between the left and right portions of the images around a selected point, such as for example point A, is performed to obtain a more accurate position estimation. The disparity and depth information are then derived using well-known analytical formulations. The depth map generated by the disparity conversion unit 90 can be further improved through a manual refinement process that removes artifacts and outliers not easily detectable by the automated aspects of the depth perception subsystem.

The present inventors have realized that the depth maps 72A, 72B, 76A, 76B, and 92 generated by the autofocus conversion units 70A, 70B, the parallax conversion units 80A, 80B, and the disparity conversion unit 90 can be intrinsically unreliable if used separately to determine distance. The individual depth maps may not include all of the necessary image data and associated position data to properly and adequately control the robotic subsystem 20. To address this unreliability, the depth perception subsystem 50 can employ a depth map conversion unit 100. The depth map conversion unit 100 is arranged to receive all of the depth maps and associated distance data generated by the depth perception subsystem 50 and combines or merges the depth maps into a single combined depth map 122. The depth map conversion unit 100 can employ one or more different types of processing techniques, including for example a regional convolution neural network (R-CNN) based encoder-decoder architecture.

Figure 4:
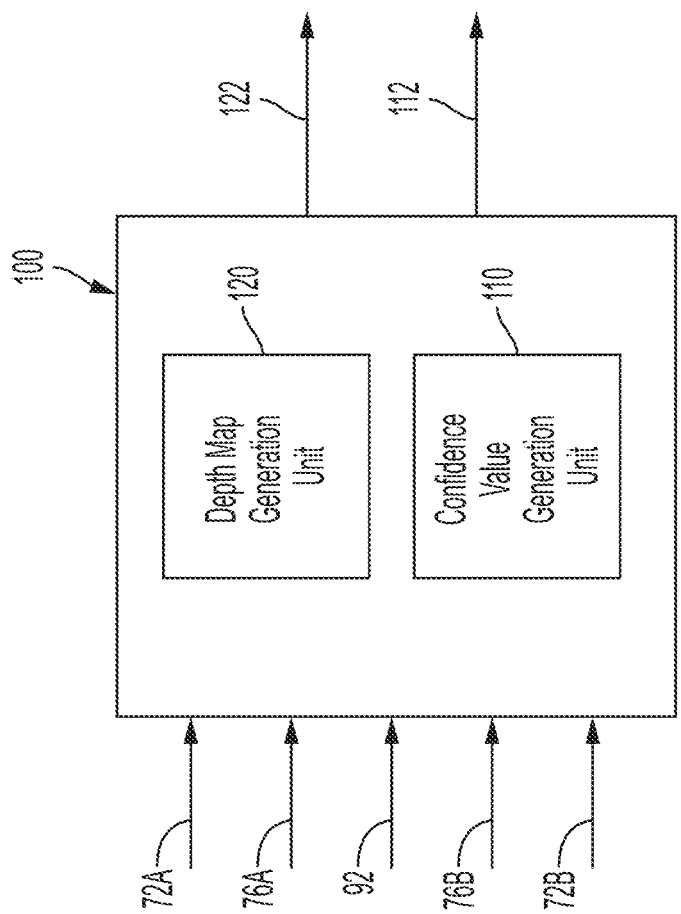
FIG. 4 is a schematic block diagram of the depth map conversion unit of the depth perception subsystem according to the teachings of the present invention.

The details of the depth map conversion unit 100 are shown in FIGS. 3 and 4. As shown in FIG. 3, the depth map conversion unit 100 can include a depth map generation unit 120 that combines the input depth maps and generates from the depth maps a single combined output depth map 122. The depth map conversion unit 100 also includes a confidence value generation unit 110 for generating one or more confidence values 112 associated with each distance or point on the depth map, or associated with a portion or segment of the depth map. As used herein, the term "confidence value" or "likelihood value" is intended to include any value that provides a way to quantify and to convey the reliability of or confidence in the correctness or trueness of a given parameter. In the current embodiment, the value is associated with confidence in a distance measurement or value, such as the distance values associated with the depth maps. The values can be expressed in any selected range, and preferably range between 0 and 1, with zero being representative of the least or smallest confidence level or value and 1 being representative of the most or highest confidence level or value. Additionally, the confidence values can be expressed as a distance or distance range for a given depth. The confidence interval can be determined through statistical analysis of the data. This statistical analysis can take into account the spread of depth values from the depth maps from the various depth cues within a given region of the combined depth map or their fluctuations over time.

Figure 5:
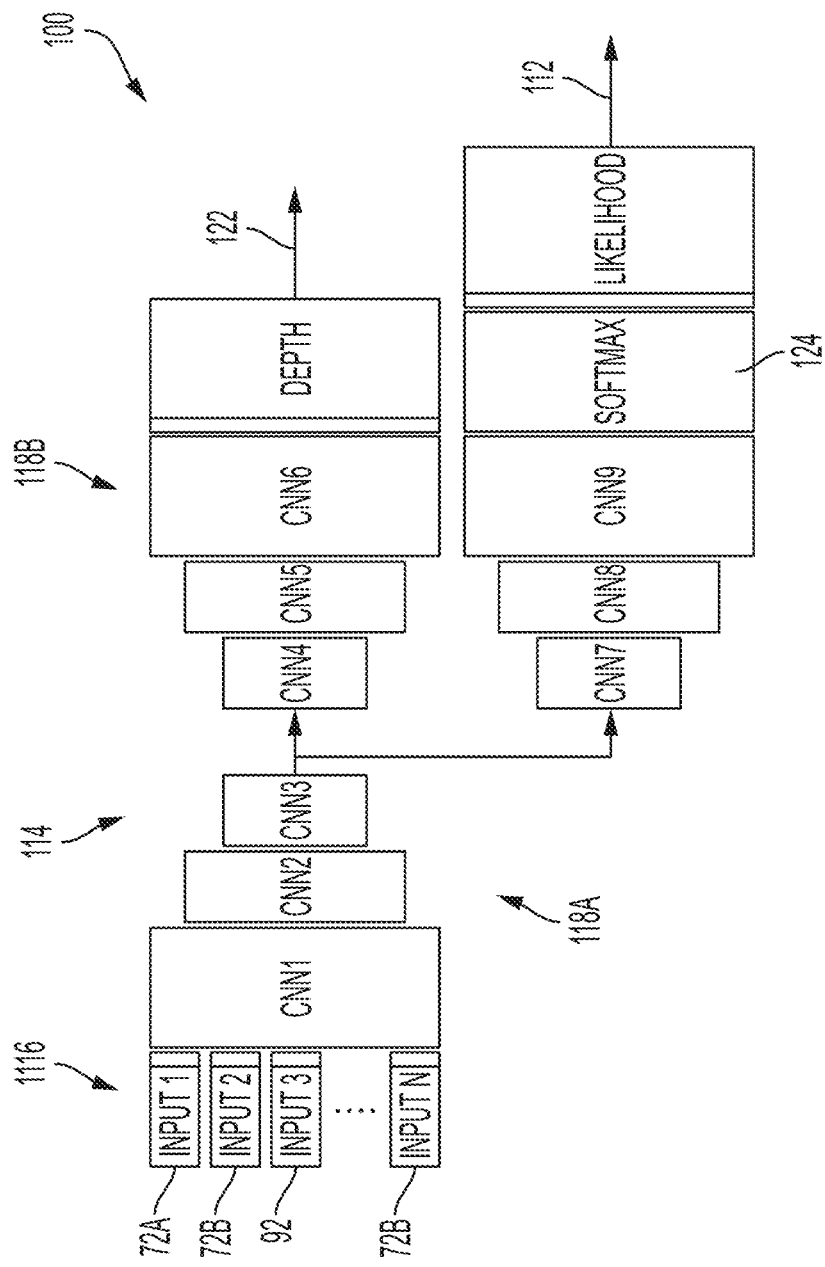
FIG. 5 is an exemplary schematic illustration of the processing technique employed by the depth map conversion unit of the depth perception subsystem according to the teachings of the present invention.

With reference to FIG. 5, the depth map conversion unit 100 can employ the regional convolution neural network (CNN) based encoder-decoder architecture 114 that imports a plurality of input data streams 116, such as the depth maps, and then processes the depth map data using a series of CNN filters or stages. The CNN filters can be arranged at the input as an encoder stage or series of CNN filters 118A where the data in the depth maps is down-sampled so as to reduce the distance and image data therein to the best or highest quality pixels or image segments. The data can then be up-sampled in a decoder stage of CNN filters 118B that employs a series of arranged CNN filters where the data is combined with other data from the input side to form or create a combined image, such as the single combined depth map 122. The encoder-decoder CNN architecture 114 helps remove noise from the input data and hence generate more accurate output data, such as the single combined depth map 122. The encoder-decoder CNN architecture 114 can also include a parallel up-sampling or decoding stage of CNN filters 18C where the input data is also up-sampled and any attendant noise is removed. The data can then be processed through a Softmax function 124 to generate or create the confidence values 112. As is known, a Softmax function is a generalization of a logistic function to multiple dimensions, and can be used in multinomial logistic regression as a last activation function of a neural network to normalize the output of a network to a probability distribution over a predicted output class. In this embodiment, the output of the Softmax function can be used to calculate the probability of the depth value for the specific point in the depth map to be accurate. The encoder-decoder CNN architecture 114 merges the input depth maps with a probabilistic approach that minimizes or reduces the noise in the single combined depth map 122 and achieves an estimate of the true distance values associated therewith that are better than the data contained in each individual input depth map. In some other embodiments, the estimation of 112, 118A can also consider any confidence data generated by 72A, 72B, 76A, 76B, and 92 during their deliberation. The encoder-decoder CNN architecture 114 can be trained using the expected output of the examples in one or more training sets of input depth or distance cues or maps, and the resulting depth and likelihood maps can be calculated analytically from the input depth maps. Other methods known in the art or combining the depth maps can also be utilized, such as for example Kalman Filters, Particle filters, and the like.

As noted above, the noise in the input depth maps can arise in different ways. For example, with regard to the auto-focus mechanisms, according to the laws of physics and optics, such as focal length and lens mechanics, the camera tends to inadvertently amplify measurement errors and hence render the estimation ineffective. The system and method of the present invention uses the depth maps 72A, 72B in conjunction with the other depth maps to remove spurious or outlier readings. Further, the noise in the calculation of disparity is generally associated with the richness of the observed environment. An abundance of unique features in the images strongly reduces the probability of ambiguity (e.g., the source of noise for this type of cue or depth map). When considered independently from other input data sources, a depth source using disparity has no recourse to resolve the ambiguity. The system of the present invention is capable of resolving this ambiguity by considering what other sources are estimating for the same region of the image and discarding the erroneous or less likely possibilities. The parallax cues or depth maps can be complex to calculate as they depend on a number of noisy parameters, such as for example the correct measurement of the actuated camera motion and knowledge of the geometrical relationships between the left and right imaging sensors 58A, 58B. With the fusion approach of the present invention, the system 10 is able to reduce the impact of the noise of this cue or depth map and produce a single combined depth map that is far less noisy that the input sources or depth maps considered individually.

Figure 6:
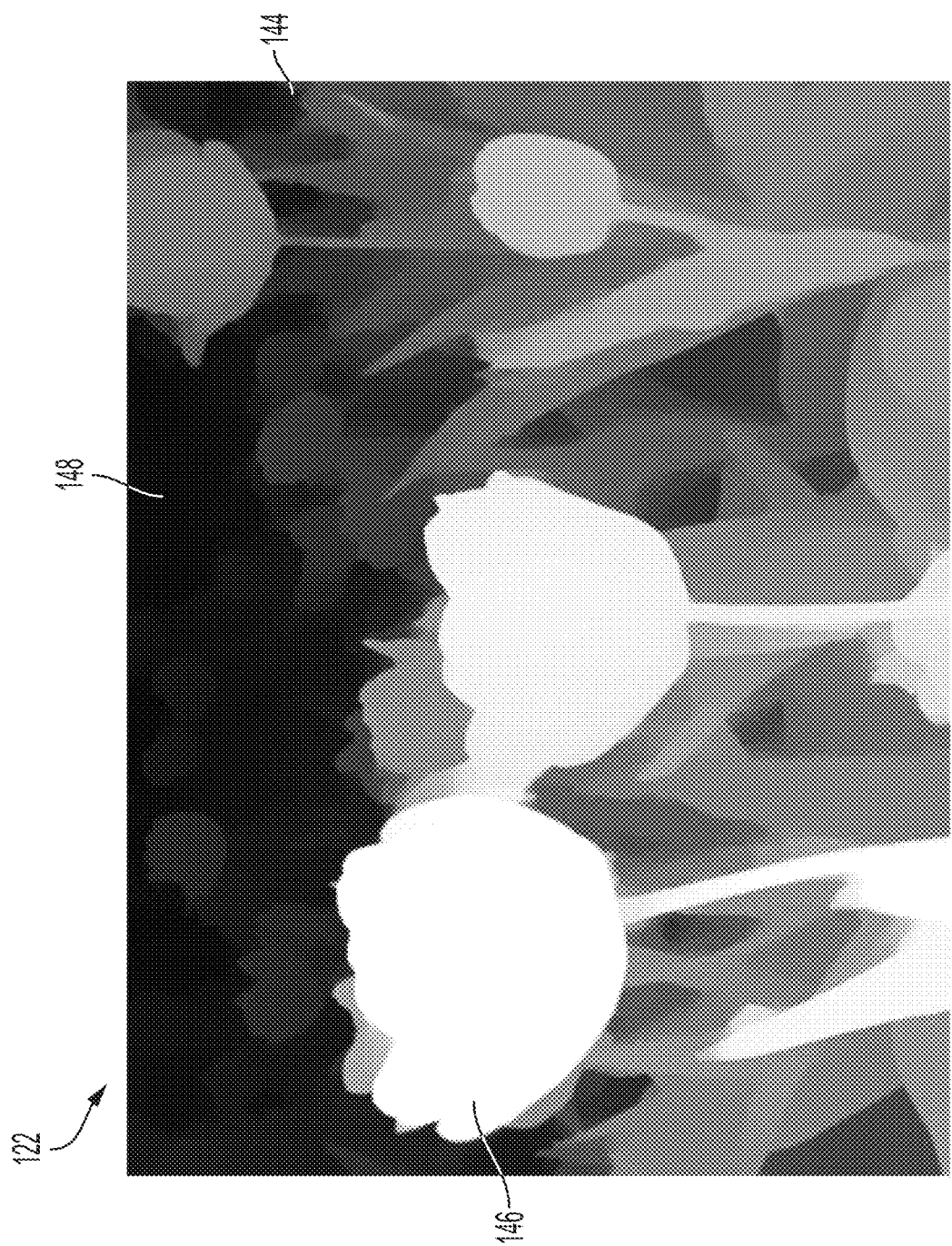
FIG. 6 is an illustration of an example depth map according to the teachings of the present invention.

FIG. 6 is an illustrative example of a combined depth map 122 that can be generated by the depth map conversion unit 100 according to the teachings of the present invention. The illustrated depth map 122 is formed by combining all of the input depth maps. The depth map 122 includes a scene 144 that includes a series of pixels forming images in the scene. The images can have various hues that are indicative of different distances or depths from a point of view. The current scene 144 is represented in gray scale, although other colors can also be used. The lighter hues 146 can be representative of pixels or segments of images in the scene 144 that are closer to the point of view, and the darker hues 148 can be representative of pixels or segments of the image that are farther from the point of view. The pixels in the depth map thus have associated therewith a distance value, the depth map generator can also generate a confidence value 112 that is associated with each distance value. Hence, each point or pixel of the depth map can have a depth value and a confidence value associated therewith. The confidence values can be stored separately in the system.

With reference again to FIG. 2, the depth map 122 and the confidence values 112 generated by the depth map conversion unit 100 can be introduced to the control unit 26. The distance values and the confidence values can be used by the control unit 26 to control movement of the cameras 44a, 44b and/or the robot arms 42 of the robotic subsystem 20. The confidence values provide a reasonable degree of confidence that if the surgeon moves, for example, the robot arms the distance indicated in the depth map 122 that the arms will not contact the surface prior to or after the distance measurement. For delicate surgical procedures, having confidence in the distance values in the depth map are important since the surgeon needs to know if the instructions sent to the robot arms and cameras are accurate. The depth maps are important for automatically warning of or preventing the surgeon from accidentally contacting the surgical environment or anatomy, thus enabling the system to automatically traverse the surgical environment and interact with anatomical components without intervention by the surgeon. Additionally, the depth perception subsystem can enable "guide rails" to be placed virtually in the surgical environment to help control and/or direct movement of the robotic subsystem. Likewise, the depth maps allow the surgical environment to be augmented or virtual objects to be more accurately placed within the environment, such as overlaying preoperative scans of the surgical site, or a patient's vitals, as disclosed or example in International Patent Application No. PCT/US2020/059137, the contents of which are herein incorporated by reference. Depth maps can also be used with computer vision and artificial intelligence to help identify anatomical structures and anomalous structures. Additionally, depth maps can be used in combination with advanced sensory information (e.g. multiple wavelength imagery to detail vasculature) or patient imagery (e.g. MRI, CAT Scan, etc.) to create rich three-dimensional maps that the surgeon can use to plan a future procedure.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

We claim:

1. A surgical robotic system, comprising:
    a robotic subsystem including a camera assembly comprising a first camera and a second camera for generating image data; and
    a computing unit including:
        a processor for processing the image data;
        a control unit for controlling the robotic subsystem; and
        a depth perception subsystem for:
            receiving the image data generated by the first and second cameras and for generating, based on the image data, a plurality of depth maps, and converting the plurality of depth maps into a single combined depth map having distance data associated therewith.

2. The surgical robotic system of claim 1, wherein the robotic subsystem further comprises:
    a plurality of robotic arms; and
    a motor unit for controlling movement of the plurality of robotic arms and the camera assembly.

3. The surgical robotic system of claim 2, wherein the control unit employs the distance data associated with the single combined depth map to control the camera assembly, the plurality of robotic arms, or both.

4. The surgical robotic system of claim 1, wherein the depth perception subsystem further comprises a depth map conversion unit for receiving the plurality of depth maps and converting the plurality of depth maps into the single combined depth map.

5. The surgical robotic system of claim 4, wherein the depth map conversion unit generates the single combined depth map using a regional convolutional neural network (R-CNN) technique.

6. The surgical robotic system of claim 1, wherein the first camera and the second camera each comprise:
    an image sensor for receiving light and for generating the image data in response thereto;
    a lens and optical system having one or more lens elements optically coupled with the image sensor for focusing the light onto the image sensor; and
    an autofocus mechanism associated with the lens and optical system for automatically adjusting the one or more lens elements and for generating autofocus data.

7. The surgical robotic system of claim 6, wherein the depth perception subsystem comprises:
    a first autofocus conversion unit for receiving the autofocus data from the first camera and for converting the autofocus data into a first autofocus depth map; and
    a second autofocus conversion unit for receiving the autofocus data from the second camera and for converting the autofocus data into a second autofocus depth map.

8. The surgical robotic system of claim 7, wherein the depth perception subsystem further comprises:
    a first parallax conversion unit for receiving image data from the first camera and for converting the image data into a first parallax depth map; and
    a second parallax conversion unit for receiving image data from the second camera and for converting the image data into a second parallax depth map.

9. The surgical robotic system of claim 8, wherein the depth perception subsystem further comprises: a disparity conversion unit for receiving image data from the first camera and image data from the second camera, and generating in response thereto a disparity depth map.

10. The surgical robotic system of claim 6, wherein the depth perception subsystem comprises one or more of:
    (a) a first autofocus conversion unit for receiving the autofocus data from the first camera and for converting the autofocus data from the first camera into a first autofocus depth map, and a second autofocus conversion unit for receiving the autofocus data from the second camera and for converting the autofocus data from the second camera into a second autofocus depth map;
    (b) a first parallax conversion unit for receiving image data from the first camera and for converting the image data from the first camera into a first parallax depth map, and a second parallax conversion unit for receiving image data from the second camera and for converting the image data from the second camera into a second parallax depth map; or
    (c) a disparity conversion unit for receiving image data from the first camera and image data from the second camera and generating in response thereto a disparity depth map based on the received image data from the first camera and the received image data from the second data.

11. The surgical robotic system of claim 10, wherein each of the first and second parallax units is configured to acquire successive first and second images in the image data and then to measure an amount that each portion of the first image moves relative to the successive second image.

12. The surgical robotic system of claim 11, wherein the first camera and the second camera each generate position data, and wherein each of the first and second parallax conversion units comprises:

a segmentation unit for receiving the image data from the respective camera and dividing the image data into a plurality of segments, and generating shifted image data based on the plurality of segments;

a movement determination unit for receiving the position data from the respective camera and generating camera movement data indicative of the position of the camera based on the received position data; and a distance conversion unit for receiving the image data and the camera movement data and converting the image data and the camera movement data into the respective parallax depth map.

13. The surgical robotic system of claim 12, wherein the distance conversion unit employs a regional convolutional neural network (R-CNN) technique to generate the respective parallax depth map.

14. The surgical robotic system of claim 10, wherein the disparity conversion unit analyzes a disparity between an image in the image data received from the first camera and an image in the image data received from the second camera.

15. The surgical robotic system of claim 14, wherein the disparity between the image in the image data received from the first camera and the image in the image data received from the second camera is determined using a layered regional convolutional neural network (R-CNN) technique.

16. The surgical robotic system of claim 10, wherein the depth perception subsystem further comprises a depth map conversion unit for:

receiving the first autofocus depth map, the second autofocus depth map, the first parallax depth map, the second parallax depth map, and the disparity depth map that form a received plurality of depth maps, and converting the received plurality of depth maps into the single combined depth map.

17. The surgical robotic system of claim 16, wherein the depth map conversion unit generates the single combined depth map using a regional convolutional neural network (R-CNN) based encoder-decoder architecture.

18. The surgical robotic system of claim 17, wherein each point in each of the received depth maps has a distance value associated therewith; and wherein the depth map conversion unit comprises:

a depth map generation unit for receiving the plurality of depth maps and for converting the received plurality of depth maps into the single combined depth map; and a confidence value generation unit for generating from the received plurality of depth maps a confidence value associated with each of the distance values associated with each point of the single combined depth map;

wherein the confidence value is indicative of a confidence in the distance values associated with the single combined depth map.

19. A method for generating a depth map from image data in a surgical robotic system, comprising:

generating image data using a robotic subsystem including a camera assembly comprising a first camera and a second camera;

generating, based on the image data from the first and second cameras, a plurality of depth maps;

converting the plurality of depth maps into a single combined depth map having distance data associated therewith; and controlling the camera assembly based on the distance data in the single combined depth map.

20. The method of claim 19, wherein the robotic subsystem further comprises a plurality of robotic arms and a motor unit for controlling movement of the plurality of robotic arms and the camera assembly; and wherein the method further comprises controlling the plurality of robotic arms based on the distance data in the single combined depth map.

21. The method of claim 19, wherein the first camera and the second camera each comprise an image sensor, a lens and optical system, and an autofocus mechanism associated with the lens and optical system; and wherein the method further comprises for each of the first camera and the second camera:

focusing light onto the image sensor of the respective first camera or second camera using one or more lens elements of the lens and optical system that are optically coupled with the image sensor;

receiving light and generating the image data in response thereto using the image sensor;

generating autofocus data for the respective first camera or second camera using the autofocus mechanism; and automatically adjusting the one or more lens elements of the respective first camera or second camera using the autofocus mechanism.

22. The method of claim 21, further comprising:

converting the generated autofocus data from the first camera into a first autofocus depth map;

converting the generated autofocus data from the second camera into a second autofocus depth map;

converting the image data from the first camera into a first parallax depth map;

converting the image data from the second camera into a second parallax depth map; and generating a disparity depth map using the image data from the first camera and the image data from the second camera.

23. The method of claim 21, further comprising one or more of:

(a) converting the generated autofocus data for the first camera into a first autofocus depth map and converting the generated autofocus data for the second camera into a second autofocus depth map;

(b) converting the generated image data from the first camera into a first parallax depth map and converting the generated image data from the second camera into a second parallax depth map; or (c) generating a disparity depth map based on the generated image data from the first camera and the generated image data from the second camera.

24. The method of claim 23, wherein converting the generated image data from the first camera into the first parallax depth map comprises acquiring successive first and second images in the image data and measuring an amount that each portion of the first image moves relative to the successive second image; and wherein converting the generated image data from the second camera into the second parallax depth map comprises acquiring successive first and second images in the image data and measuring an amount that each portion of the first image moves relative to the successive second image.

25. The method of claim 23, wherein the first camera and the second camera generate position data; and
wherein converting the generated image data from the first camera into the first parallax depth map comprises:
dividing the image data from the first camera into a first plurality of segments;
generating first shifted image data based on the first plurality of segments;
generating first camera movement data based on the position data from the first camera; and
converting the first shifted image data from the first camera and the first camera movement data into the first parallax depth map; and
wherein converting the generated image data from the second camera into the second parallax depth map comprises:
dividing the image data from the second camera into a second plurality of segments;
generating second shifted image data based on the second plurality of segments;
generating second camera movement data based on the position data from the second camera; and
converting the second shifted image data from the second camera and the second camera movement data into the second parallax depth map.

26. The method of claim 23, wherein generating the disparity depth map based on the generated image date from the first camera and the generated image data from the second camera comprises analyzing a disparity between an image in the image data received from the first camera and an image in the image data received from the second camera.

27. The method of claim 23, further comprising: receiving the first autofocus depth map, the second autofocus depth map, the first parallax depth map, the second parallax depth map, and the disparity depth map that form a received plurality of depth maps; and
converting the received plurality of depth maps into the single combined depth map.

28. The method of claim 27, wherein each point in each of the received plurality of depth maps has a distance value associated therewith; and
wherein the method further comprises generating from the received plurality of depth maps a confidence value associated with each of the distance values associated with each point of the single combined depth map, wherein the confidence value of each distance value is indicative of a confidence in the distance value associated with the single combined depth map.

* * * * *